United States Patent
Roberts

(10) Patent No.: US 6,913,017 B2
(45) Date of Patent: Jul. 5, 2005

(54) APPARATUS FOR DELIVERING INHALANT AND MONITORING EXHALED FLUID, METHOD OF MAKING SAME, AND METHOD OF DELIVERING INHALANT AND MONITORING EXHALED FLUID

(76) Inventor: Bevely Roberts, 20326 Beaverland, Detroit, MI (US) 48219

( * ) Notice: Subject to any disclaimer, the term of this patent is extended or adjusted under 35 U.S.C. 154(b) by 163 days.

(21) Appl. No.: 10/035,166

(22) Filed: Jan. 4, 2002

(65) Prior Publication Data

US 2003/0127094 A1 Jul. 10, 2003

(51) Int. Cl.$^7$ .............................................. A61M 15/08
(52) U.S. Cl. ............................. 128/207.18; 128/206.11; 128/DIG. 26
(58) Field of Search ...................... 128/207.18, 206.11, 128/DIG. 26

(56) References Cited

U.S. PATENT DOCUMENTS

| | | | |
|---|---|---|---|
| 4,256,099 A | | 3/1981 | Dryden |
| 4,300,550 A | | 11/1981 | Gandi et al. |
| 4,363,323 A | | 12/1982 | Geiss |
| 4,446,869 A | * | 5/1984 | Knodle ........................ 600/529 |
| 4,808,160 A | * | 2/1989 | Timmons et al. ......... 604/94.01 |
| 4,821,715 A | | 4/1989 | Downing |
| 4,989,599 A | | 2/1991 | Carter |
| 5,046,491 A | | 9/1991 | Derrick |
| 5,131,387 A | | 7/1992 | French |
| 5,137,017 A | * | 8/1992 | Salter ..................... 128/207.18 |
| 5,335,656 A | | 8/1994 | Bowe |
| 5,555,890 A | | 9/1996 | Schaller |
| 5,682,881 A | | 11/1997 | Winthrop et al. |
| 5,937,858 A | | 8/1999 | Connell |
| 6,098,617 A | | 8/2000 | Connell |
| 6,183,493 B1 | | 2/2001 | Zammit |
| 6,186,142 B1 | * | 2/2001 | Schmidt et al. ......... 128/204.23 |
| 6,213,955 B1 | * | 4/2001 | Karakasoglu et al. ....... 600/259 |
| 6,247,470 B1 | | 6/2001 | Ketchedjian |
| 6,422,240 B1 | * | 7/2002 | Levitsky et al. ........ 128/207.18 |
| 6,439,234 B1 | * | 8/2002 | Curti et al. ............ 128/207.18 |

* cited by examiner

*Primary Examiner*—Glenn K. Dawson
*Assistant Examiner*—Darwin P Erezo
(74) *Attorney, Agent, or Firm*—Dykema Gossett PLLC

(57) ABSTRACT

(1) An apparatus for delivering inhalant and monitoring exhaled fluid; (2) a method of making same; and (3) a method of delivering inhalant and monitoring exhaled fluid are disclosed. The apparatus for delivering inhalant to and monitoring exhaled fluid from a patient includes a first cannula having a distal end adapted to be received at a first depth in, for delivering a fluid into, a nostril of the patient, and a second cannula having a distal end adapted to be received at a second depth in, for sampling exhaled fluid from, the nostril. The method of making an apparatus for delivering inhalant and monitoring exhaled fluid involves modifying an apparatus, including a first cannula connected for delivering fluid to a nasal cannula, and a second cannula connected to, for drawing fluid from, the nasal cannula, which includes disconnecting the nasal cannula from the first cannula, thereby defining a first truncated end, disconnecting the nasal cannula from the second cannula, thereby defining a second truncated end, and providing one or both of the first truncated end and the second truncated end with: an aperture, a perforated zone, a rounded contour, an anesthetic coating or combinations thereof. The method of delivering inhalant to and monitoring exhaled fluid from a patient includes inserting to a first depth a distal end of a first cannula in, for delivering a fluid into, a nostril of the patient, and inserting to a second depth a distal end of a second cannula in, for sampling exhaled fluid from, the nostril.

4 Claims, 2 Drawing Sheets

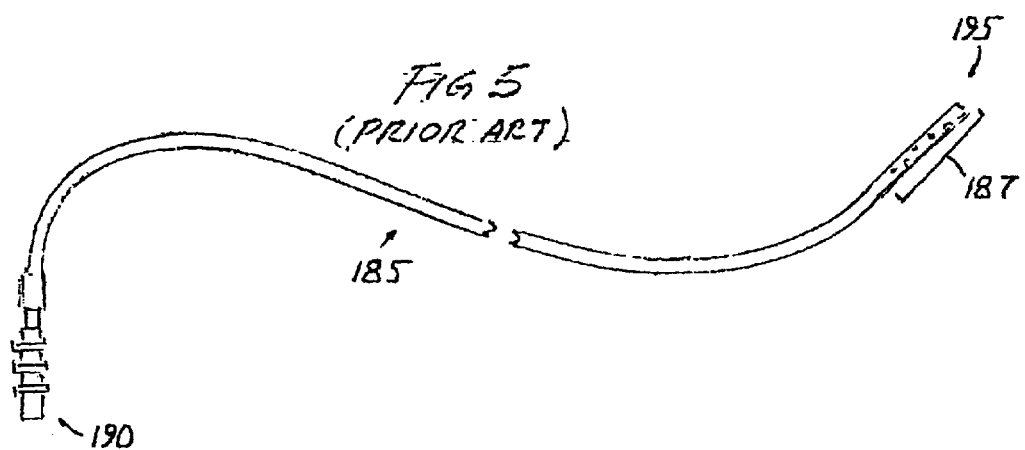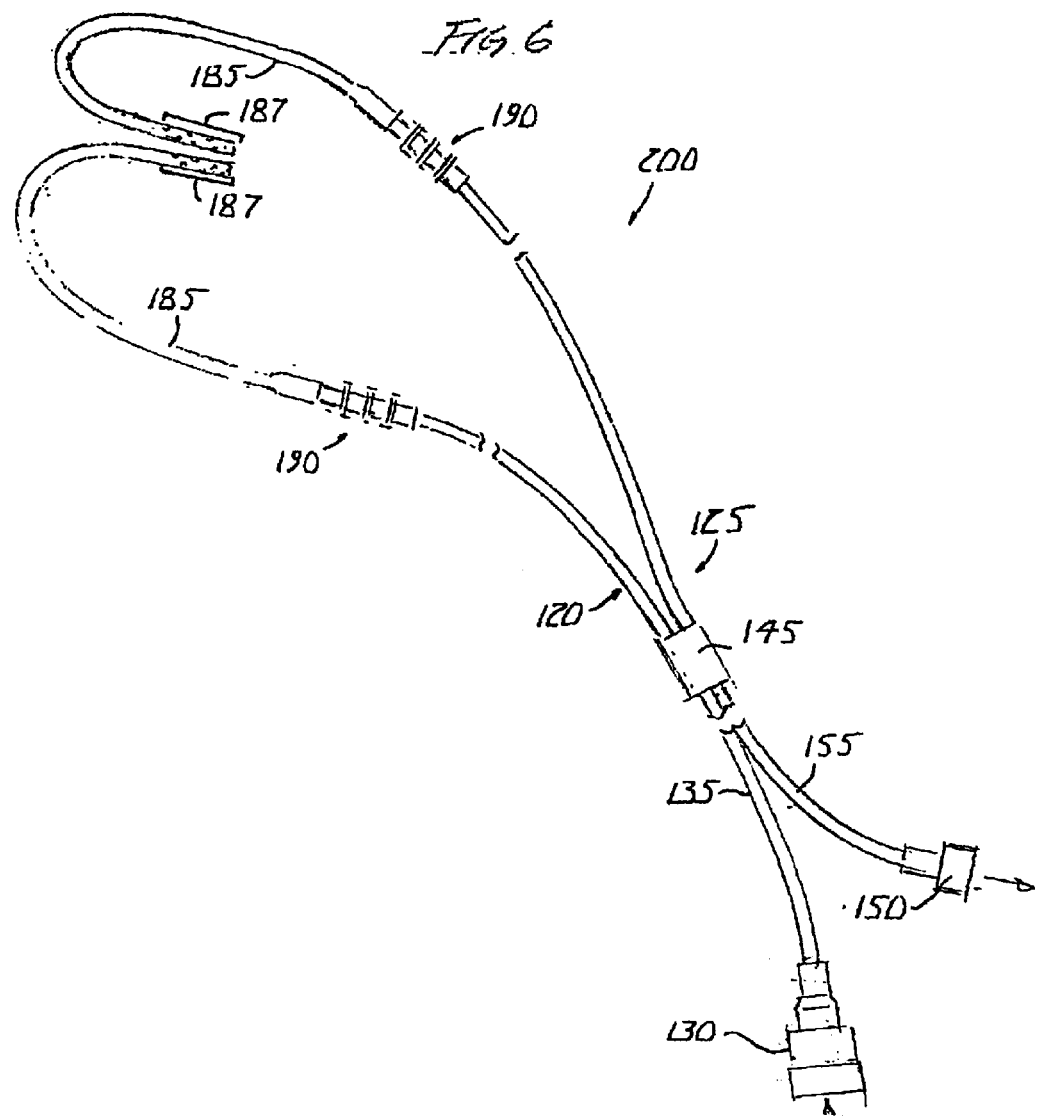

APPARATUS FOR DELIVERING INHALANT AND MONITORING EXHALED FLUID, METHOD OF MAKING SAME, AND METHOD OF DELIVERING INHALANT AND MONITORING EXHALED FLUID

BACKGROUND OF THE INVENTION

During some surgical procedures, the surgical patient is placed under general anesthesia To administer a general anesthesia, an anesthesiologist or nurse anesthetist continuously administers a general anesthetic, such as isoflurane and/or a muscle relaxant, and manages the patient's respiration. Often, the anesthesiologist or nurse anesthetist inserts an endotracheal tube into the patient's trachea for administering anesthesia. In some cases, a mechanical ventilator pumps oxygen into the patient's lungs and allows expired carbon dioxide to escape.

To ensure that proper ventilation is taking place, the anesthesiologist or nurse anesthetist typically monitors the levels of oxygen saturation in the patient's blood and the expired carbon dioxide. Pulse oximetry is the technique most often used to detect the level of blood oxygenation, and capnography commonly is used to monitor the expired carbon dioxide level. Of the two types of monitors for detecting proper ventilation, the carbon dioxide monitor is far quicker to indicate an interruption of ventilation since oxygen saturation can remain at a normal or near normal level for several minutes after proper ventilation has ceased. On the other hand, ventilation interruption will immediately give rise to a precipitous drop in the carbon dioxide level.

An increasingly popular alternative to general anesthesia is Monitored Anesthesia Care (MAC) with intravenous sedation. MAC differs from general anesthesia in that MAC involves shorter-acting anesthetics, such as propofol or midazalam, which place the patient in a deep state of anesthesia. A ventilator does not assist the patient, rather the patient breathes self-sufficiently, as if sleeping.

Although shorter acting, MAC drugs are effective hypnotics and analgesics. As a result, MAC has been able to be used for increasingly more surgical procedures that formerly had been performed under general anesthesia. This increases the number of surgeries that may be performed on an out-patient basis.

During MAC anesthesia procedures, oxygen commonly is delivered to the patient either through a facial mask or through a nasal cannula. Either of such delivery devices enables the patient to achieve oxygenation. As in the case of general anesthesia, oxygen saturation commonly is measured by pulse oximetry, using an infrared sensor typically attached to the patient's finger, ear or toe. When a mask is used for administering oxygen, the level of expired carbon dioxide can be monitored easily by placing a capnograph sample line inside the mask. When a nasal cannula is used for administering oxygen, one of the two nasal prongs can be connected to the capnograph sample line while the other prong supplies oxygen.

While both the facial mask and the nasal cannula can be highly effective in delivering oxygen and monitoring expired gas, both can be problematic under certain circumstances. For example, a facial mask can interfere with surgical procedures involving the patient's face, thus usually is not used during such procedures. On the other hand, a split nasal cannula can only be used when both nasal passages are clear. When either nasal passage is closed or even partially obstructed, either oxygen delivery or carbon dioxide monitoring is compromised.

During MAC with sedation procedures, a patient may become so sedate that breathing slows or even stops all together. When a respiration failure occurs, for example due to an obstruction or closure of the patient's airway when the patient's tongue falls back in the pharynx, the anesthesiologist or nurse anesthetist must respond quickly to restore respiration. Usually, the anesthesiologist or nurse anesthetist can restore proper breathing by manipulating the patient's jaw or repositioning of the patient's head. However, sometimes the anesthesiologist or nurse anesthetist must install a mechanical "airway" in the patient's pharynx, either through the mouth or nose, to clear the obstruction.

A typical mechanical airway includes a soft rubber tube having a length sufficient to pass any obstruction in the pharynx and to allow normal respiratory gas exchange through the tube. Usually, such airways have an arcuate shape to conform to the shape of the oral/nasal pharynx. Mechanical airways are quite uncomfortable to conscious patients. Thus, absent critical need, mechanical airways typically are used after the patient is sedated.

Some surgical procedures do not require the deep state of anesthesia obtained from a general anesthetic; MAC procedures or local anesthetic with intravenous sedation are adequate. Local anesthesia involves topical application or injection of a numbing agent, or local nerve depressant, that acts within a zone about the anesthetic application site. Intravenous sedation involves the administration of a drug, such as benzodiazepines or a narcotic, which results in the depression of the central nervous system. However, the objective of intravenous sedation is to produce a degree of sedation whereby rational verbal communication to and from the patient is possible. The drugs and techniques used are calculated to render unintended loss of consciousness unlikely. Thus, intravenously sedated patients tend to be semi-conscious, not completely unconscious.

Surgeons who perform facial plastic surgical procedures, and more specifically, facial reconstruction and rhinoplasty, prefer to employ local anesthetic with intravenous sedation. To avoid obscuring, cluttering or obstructing the surgical field, as well as limit patient discomfort, surgeons avoid the use of anesthetizing masks and minimize the size and number cannulae needed for administering sedation. However, available devices typically are received in and/or fully occlude one or both nostrils of a patient, interfering with the surgical field. Other available devices include mechanical airways that cause discomfort to conscious patients, thus are not amenable to intravenous sedation.

What are needed, and not taught or suggested by prior devices and techniques, are: (1) an apparatus for delivering inhalant and monitoring exhaled fluid; (2) a method of making same; and (3) a method of delivering inhalant and monitoring exhaled fluid.

SUMMARY OF THE INVENTION

The invention provides (1) an apparatus for delivering inhalant and monitoring exhaled fluid, (2) a method of making same; and (3) a method of delivering inhalant and monitoring exhaled fluid. The apparatus for delivering inhalant to and monitoring exhaled fluid from a patient includes a first cannula having a distal end adapted to be received at a first depth in, for delivering a fluid into, a nostril of the patient, and a second cannula having a distal end adapted to be received at a second depth in, for sampling exhaled fluid from, the nostril. The method of making an apparatus for delivering inhalant and monitoring exhaled fluid involves modifying an apparatus, including a first cannula connected for delivering fluid to a nasal cannula, and a second cannula connected to, for drawing fluid from, the nasal cannula, and includes disconnecting the nasal cannula from the first cannula, thereby defining a first truncated end, disconnecting the nasal cannula from the second cannula, thereby defining a second truncated end, and providing one or both of the first truncated end and the second truncated end with: an aperture, a perforated zone, a rounded contour, an anesthetic coating or combinations thereof. The method of delivering inhalant to and monitoring exhaled fluid from a patient includes inserting to a first depth a distal end of a first cannula in, for delivering a fluid into, a nostril of the patient, and inserting to a second depth a distal end of a second cannula in, for sampling exhaled fluid from, the nostril.

The invention provides improved elements and arrangements thereof, for the purposes described, which are inexpensive, dependable and effective in accomplishing intended purposes of the invention. Other features and advantages of the present invention will become apparent from the following description of the preferred embodiments which refers to the accompanying drawings.

BRIEF DESCRIPTION OF THE DRAWINGS

The invention is described in detail below with reference to the following figures, throughout which similar reference characters denote corresponding features consistently, wherein:

FIG. 5 is a plan view of a prior art cannula; and

FIG. 6 is a plan view of an another embodiment of an apparatus for delivering inhalant and monitoring exhaled fluid constructed according to principles of the invention.

DETAILED DESCRIPTION OF THE PREFERRED EMBODIMENTS

The invention is (1) an apparatus for delivering inhalant and monitoring exhaled fluid, (2) a method of making same; and (3) a method of delivering inhalant and monitoring exhaled fluid. Preferably, although not exclusively, the invention may be employed during administering intravenous sedation of a surgical patient. The apparatus provides for delivering a fluid, including gases, liquids or other flowable materials, such as gaseous oxygen, to the patient. The apparatus also provides for sampling a fluid, including gases, liquids or other flowable materials, such as gaseous carbon dioxide, exhaled by the patient. The device minimizes discomfort for a conscious patient.

Figure 1:
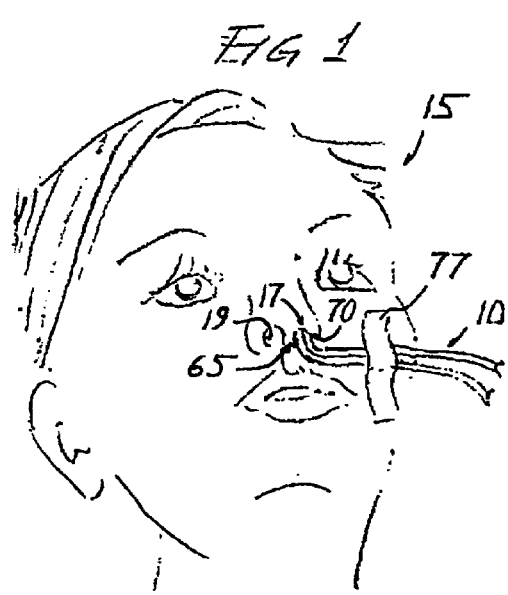
FIG. 1 is an environmental perspective view of the apparatus of FIG. 2 positioned for delivering inhalant to and monitoring exhaled fluid from a patient.

FIG. 1 shows a portion of the present apparatus 10 positioned for delivering inhalant to and monitoring exhaled fluid from a patient 15. Consistent with typical intravenous sedation practices, patient 15 is conscious. While conscious, patient 15 tolerates the minimal invasiveness of apparatus 10. However, patient 15 will not tolerate more invasive devices, such as that of U.S. Pat. No. 5,937,858.

Figure 2:
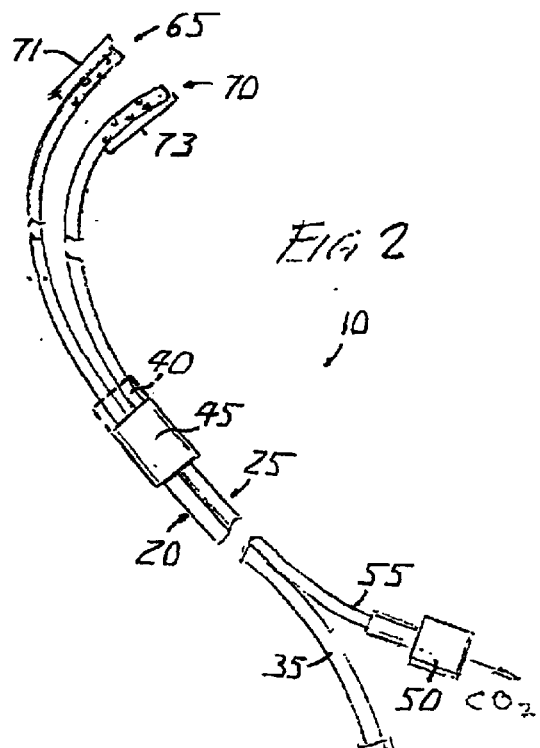
FIG. 2 is a plan view of an embodiment of an apparatus for delivering inhalant and monitoring exhaled fluid constructed according to principles of the invention.

Referring to FIG. 2, apparatus 10 has a fluid delivery conduit assembly 20 and a fluid sampling conduit assembly 25. Fluid delivery conduit assembly 20 and fluid sampling conduit assembly 25 may be bundled or relatively fixed for convenient handling with a stabilizer 45. However, stabilizer 45 is only for convenience and is not required for apparatus 10 to perform intended functions.

Fluid delivery conduit assembly 20 includes a port 30 configured to connect with equipment (not shown) for supplying a fluid, such as gaseous oxygen, to patient 15. Port 30 is sealingly connected, for delivering the fluid, to a delivery cannula 35. Port 30 is conventional in the art.

Fluid sampling conduit assembly 25 includes a port 50 configured to connect with equipment (not shown) for sampling or analyzing a fluid, such as exhaled fluid from patient 15, to ascertain concentration of, for example, gaseous carbon dioxide. Port 50 is sealingly connected to, for receiving the fluid from, a receiving cannula 55. Port 50 is conventional in the art.

Each distal end 65 and 70 respectively of delivery cannula 35 and receiving cannula 55 terminate in an aperture and/or have respective perforated zones 71 and 73. The terminal aperture and perforated zones, or any other appropriate structures, are intended to facilitate delivery or sampling of fluid, and prevent interruption of same due to blockage of distal ends 65 and 70 by tissue or other debris.

Referring again to FIG. 1, apparatus 10 may be used during administering intravenous sedation of a conscious or semi-conscious patient 15. To limit patient discomfort, as well as avoid obscuring, cluttering or obstructing the surgical field, distal ends 65 and 70 both are inserted in one nostril 17 of patient 15, to a depth ranging up to approximately 3 cm. Thus, patient 15 does not experience discomfort from the natural body reactions to foreign objects sensed in passageways, such as a nasal airway. To further avoid or alleviate patient discomfort, distal ends 65 and 70 may be provided with a rounded contour and/or coated with an anesthetic gel.

Preferably, distal end 70, for sampling exhaled breath, is disposed deeper in nostril 17 than distal end 65. This averts obtaining faulty fluid sampling results which otherwise might occur if fluid were permitted to be delivered from distal end 65 upstream of distal end 70 when patient 15 exhales.

Delivery cannula 35 and receiving cannula 55 may be arranged on and secured to patient 15 in any manner, such as with tape 77 that directly adheres to patient 15, delivery cannula 35 and receiving cannula 55, thereby fostering fluid delivery and sampling, without obstructing the surgical field. Because distal ends 65 and 70 both are inserted in one nostril 17, the other nostril 19, which may be an object of the surgery, is unobstructed.

Referring again to FIG. 2, an alternative embodiment of apparatus 10 includes a conventional moisture trap 40. A typical moisture trap may, but is not limited to, include a hydrophilic material contained within a housing for separating moisture from the patient's exhalations prior to those exhalations reaching a monitoring device. Sometimes a hydrophobic member is positioned in the flow path of the exhalations to occlude and interrupt the flow path when the hydrophilic material becomes saturated and no longer is capable of absorbing moisture. See, for example, U.S. Pat. No. 5,131,387, which is incorporated herein.

Figure 3:
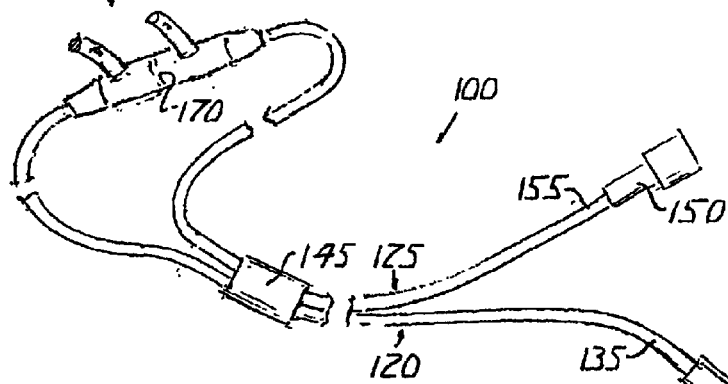
FIG. 3 is a plan view of a prior art apparatus for delivering inhalant and monitoring exhaled fluid.

Referring to FIGS. 3–6, the invention provides for modifying an existing apparatus 100, as shown in FIG. 3, and combining same with another apparatus 185, as shown in FIG. 5, to achieve an apparatus 200, as shown in FIG. 6, which functions comparably to apparatus 10, as shown in FIG. 1. Similar to apparatus 10, apparatus 100 has a fluid delivery conduit assembly 120 and a fluid sampling conduit assembly 125. Fluid delivery conduit assembly 120 and fluid sampling conduit assembly 125 are bundled or relatively fixed for convenient handling with a stabilizer 145.

Fluid delivery conduit assembly 120 includes a port 130 configured to connect with equipment (not shown) for supplying a fluid, such as gaseous oxygen. Port 130 is sealingly connected, for delivering the fluid, to a delivery cannula 135. Delivery cannula 135 is sealingly connected, for delivering the fluid, to a nasal cannula 165, as described in U.S. Pat. No. 5,335,656. Nasal cannula 165 has a septum 170 for bifurcating fluid delivery conduit assembly 120 and fluid sampling conduit assembly 125.

Fluid sampling conduit assembly 125 includes a port 150 configured to connect with equipment for sampling and/or analyzing fluid, to ascertain, for example, carbon dioxide content. Port 150 is sealingly connected to, for receiving fluid from, a receiving cannula 155. Receiving cannula 155 is sealingly connected to, for receiving fluid from, nasal cannula 165.

Figure 4:
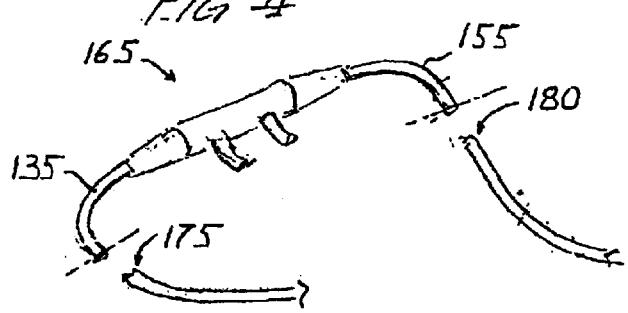
FIG. 4 is a plan view, drawn to an enlarged scale, of a portion of the apparatus of FIG. 3.

Referring also to FIG. 4, modifying apparatus 100 to achieve apparatus 200 basically involves substituting for nasal cannula 165 two cannulae, each having a distal end with structure comparable to distal ends 65 and 70 of apparatus 10. Specifically, severing delivery cannula 135 yields truncated end 175. Severing receiving cannula 155 yields truncated end 180. Next, either of truncated end 175 or truncated end 180 is inserted in and sealingly connected with the proximal end 190 of an existing cannula 185, shown in FIG. 6. The other of truncated end 175 and truncated end 180 then is inserted in and sealingly connected with the proximal end 190 of another existing cannula 185. Each cannula 185 has a distal end 195 configured to function like distal ends 65 and 70 of apparatus 10, that is, with a terminal aperture and/or perforated zone 187. As with apparatus 10, to further avoid or alleviate patient discomfort, each distal end 195 may be provided with a rounded contour and/or coated with an anesthetic gel. Modifying apparatus 100 as described yields apparatus 200, as shown in FIG. 6, which performs in a manner that corresponds with apparatus 10, as shown in FIG. 2. Other than as described herein, apparatus 200 retains elements of apparatus 100, as described above.

As with apparatus 10, an alternative embodiment of apparatus 200 includes a conventional moisture trap (not shown).

Although the invention has been described in relation to particular embodiments thereof, many other variations and modifications and other uses will become apparent to those skilled in the art. The invention is not limited by the specific disclosure herein, but only by the appended claims.

I claim:

1. Method of delivering inhalant to and monitoring exhaled fluid from a patient comprising:

inserting to a first depth a distal end of a first cannula in, for delivering a fluid into, a nostril of the patient; and inserting to a second depth a distal end of a second cannula in, for sampling exhaled fluid from, the nostril.

wherein said first and second cannulae being disposed adjacent each other, and a predefined length of said first cannula being disposed substantially separate and independent from a predefined length of said adjacently disposed second cannula, such that upon insertion into the patient's nostril, said predefined lengths of each cannula being allowed to substantially separately and independently conform to internal contours of the patient's nostril and air passage, and said predefined lengths of each cannula being substantially separately and independently disposable in contact with the internal contours of the patient's nostril and air passage.

2. Method of claim 1, wherein the first depth and second depth range up to 3 cm.

3. Method of claim 1, wherein the second depth equals or exceeds the first depth.

4. Method of claim 1, further comprising, prior to one or both of said inserting to a first depth and said inserting to a second depth, providing one or both of the distal end of the first cannula and the distal end of the second cannula with: an aperture, a perforated zone, a rounded contour, an anesthetic coating or combinations thereof.

* * * * *